United States Patent [19]

Webb

[11] Patent Number: 4,726,681

[45] Date of Patent: * Feb. 23, 1988

[54] MONITORING DEFLOCCULATED PARTICLES IN A SUSPENSION

[75] Inventor: Terence W. Webb, Cornwall, England

[73] Assignee: E.C.C. International Limited, United Kingdom

[*] Notice: The portion of the term of this patent subsequent to Dec. 9, 2003 has been disclaimed.

[21] Appl. No.: 711,998

[22] Filed: Mar. 14, 1985

[30] Foreign Application Priority Data

Mar. 15, 1984 [GB] United Kingdom ................. 8406835

[51] Int. Cl.[4] ..................... G01N 21/00; G01N 21/47; G01N 21/51
[52] U.S. Cl. .................................. 356/338; 356/343; 356/344
[58] Field of Search ............... 356/337, 338, 339, 340, 356/341, 342, 343, 344, 410, 411, 246

[56] References Cited

U.S. PATENT DOCUMENTS 3,692,412  9/1972  Chubb ................................ 356/338
4,011,044  3/1977  Uzgiris ................................ 356/344
4,113,596  9/1978  Treille et al. ....................... 356/344
4,627,727  12/1986  Jennings et al. .................... 356/338

*Primary Examiner*—R. A. Rosenberger
*Attorney, Agent, or Firm*—Stefan J. Klauber

[57] ABSTRACT

A method of monitoring the deflocculation of particles in a suspension, which particles, when deflocculated, are such that they can become aligned in an applied field, comprises applying a beam of radiation to a region of the suspension, applying a field to the region and detecting a change, if any, in radiation scattering properties of said region due to the aligning of deflocculated particles if any, of the suspension in the field, the method comprising applying such a field to such a region of a first sample of suspension whose degree of deflocculatin is desired to be monitored and applying such a field to such a region of a second sample of suspension, whose particles are known to be substantially fully deflocculated, detecting the change in radiation scattering properties of each region due to the field to produce a respective output indication, and comparing the indications to produce an indication related to the degree of deflocculation of the particles in the first suspension.

14 Claims, 12 Drawing Figures

MONITORING DEFLOCCULATED PARTICLES IN A SUSPENSION

Clays are normally mined from the ground in an aggregated, or flocculated, state. They must be disaggregated, or deflocculated, into their constituent clay mineral particles in order for further refining and particle size separation to be carried out. In the case of kaolinite, these primary particles are discs with a regular, hexagonal shape. This change in morphology, from the flocculated clay in some amorphous or spherical configuration, to the deflocculated clay with its disc shape, led to the belief that electro-optic methods would provide a novel solution to the present industrial problem of determining the state of deflocculation of concentrated aqueous suspensions of kaolinite.

As early as 1954, electric birefringence was being used to study the physical properties of clay minerals as a function of exchangeable cations (Khan, A. and Lewis, D. R., J. Phys. Chem., 58 (10), 801-804).

In 1959, electric birefringence was used to study the mechanism of flocculation of clay suspensions by polyelectrolytes (Khan, A., Proc. Natl. Conf. Clays, Clay Minerals, 6th Berkeley, 220).

According to the present invention, there is provided a method of monitoring the deflocculation of particles in a suspension, which particles, when deflocculated, are such that they can become aligned in an applied field, the method comprising applying a beam of radiation to a region of the suspension, applying a field to the said region and detecting a change, if any, in radiation scattering properties of said region due to the aligning of deflocculated particles, if any, of said suspension in said field, the method further comprising applying such a field to such a region of a first sample of suspension whose degree of deflocculation is desired to be monitored and applying such a field to such a region of a second sample of suspension, whose particles are known to be substantially fully deflocculated, detecting the change in radiation scattering properties of each region due to the field to produce a respective output indication, and comparing the indications to produce an indication related to the degree of deflocculation of the particles in the first suspension.

The said field could be an electric field, such as an alternating electric field, or it could be an acoustic or a magnetic field.

The present invention will now be described, by way of example, with reference to the accompanying drawings, in which.

Figure 1:
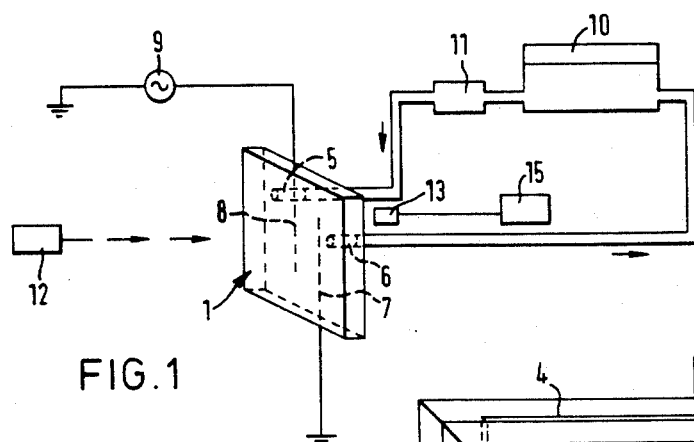
FIG. 1 is a schematic diagram of apparatus for monitoring deflocculated particles in a suspension.
Figure 2:
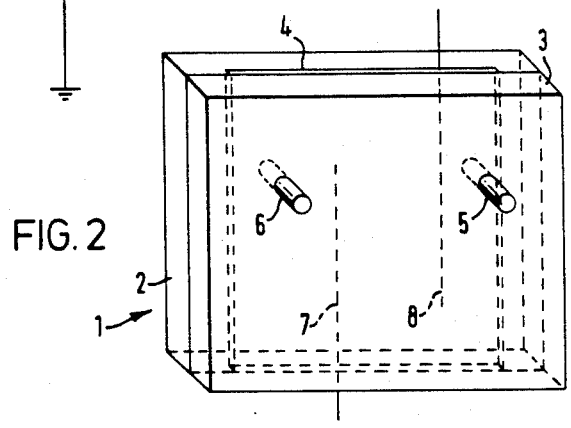
FIG. 2 shows a cell of the apparatus.
Figure 3:
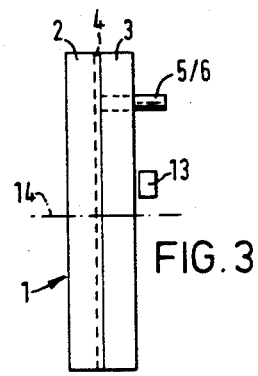
FIGS. 3 and 4 are side views of the cell with different photo-detector configurations.
Figure 4:
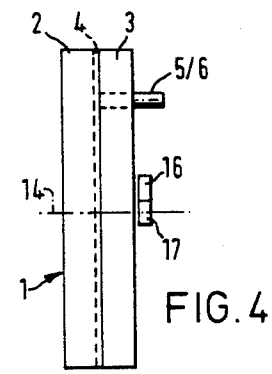

Referring to FIGS. 1, 2, 3 and 4, reference numeral 1 designates a glass cell made of two joined-together glass parts 2 and 3, there having been cut out from the part 2 in the side which faces part 3 a rectangular portion, so that there is provided a rectangular chamber 4 in the cell 1. The cell is further provided with inlet and outlet ports 5 and 6 which communicate with the chamber 4. The thickness of the cell 1 is about 4 mm and the major sides of the cell 1 are about 300 mm $\times$ 300 mm. The chamber 4 is about 0.1 mm in depth.

A pair of conductors 7 and 8 extend into the chamber 4 and overlap in a middle region thereof, the conductors 7 and 8 being about 33 mm apart, although this spacing is shown relatively wider in the Figures for the sake of clarity. A source 9 of alternating current is connected between the conductors 7 and 8, the source being for example a 50 Hz, 100 to 240 volts A.C. source for providing an alternating electric field in the chamber 4 between the conductors 7 and 8.

A suspension of kaolin in water is pumped from a reservoir 10 through the chamber 4 via the ports 5 and 6 and back to the reservoir using a pump 11, such as peristaltic pump.

Light from a laser 12, such as a helium-neon or argon laser, is directed to the centre of the cell 1 and on the opposite side of the cell from the laser, there is a photo-detector 13 in the form of a photo-diode with a built-in amplifier, although other forms of photo-detectors could be used. The photo-diode 13 is offset from the axis of symmetry 14 along which the beam from the laser 12 is directed (see FIG. 3). The amplified output, if any, from the photo-diode 13 is passed to a device 15 for processing this output.

Figure 5:
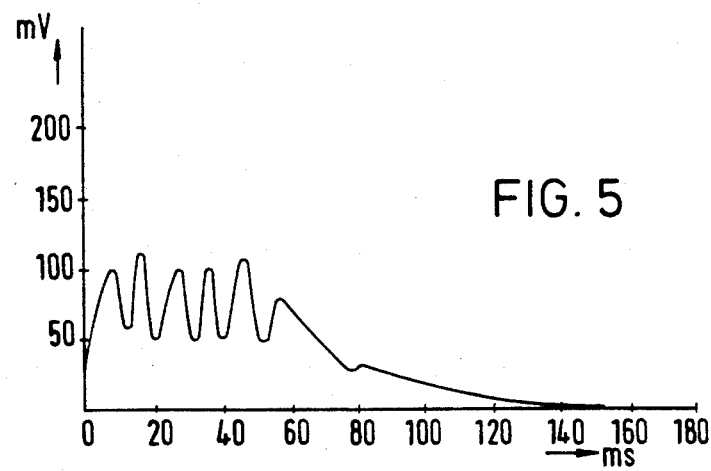
FIG. 5 is a graph showing a typical output from the apparatus for deflocculated particles.

Typically, the kaolin in the suspension from the reservoir 10 is about 30% by weight of the suspension and, if the kaolin is completely flocculated, there is substantially no output from the photo-diode 13 when the alternating electric field occurs in the chamber 4, the beam of light from the laser 12 passing straight through the cell 1, by-passing the photo-diode 13. However, if at least some of the kaolin in the suspension is deflocculated, then, in the presence of the alternating electric field, the deflocculated kaolin particles will align themselves in the field and cause scattering of the beam of light from the laser 12. Such scattering is termed transient electric field light scattering, and scattered light is detected by the photo-diode 13 so that an output is provided to the device 15. (Transient electric field light scattering is described in the paper by Plummer, H. and Jennings, B. R., J. Chem. Phys, 50 (2), 1033-1034, 1969). With a kaolin suspension of which the kaolin is about 24% by weight with at least some of it deflocculated, using for the photo-diode 13 a photo-diode with a built-in amplifier made by Centronics of type OSD15T, and with a voltage from source 9 of 240 volts A.C. at 50 Hz, there was obtained an output from the photo-diode 13 as shown by the graph of FIG. 5. The oscillatory portion of the output is due to the transient electric field light scattering and the frequency of oscillation is substantially 100 Hz, that is substantially twice the frequency of the alternating electric field. The mean peak to peak voltage of the oscillatory part of the output is a function of the degree of deflocculation of the kaolin suspension.

Instead of having a single photo-detector, offset from the axis of symmetry 14 of the cell 1 along which the beam from the laser is directed, there could be also a further photo-detector, on the same side, which photo-detector is on the axis 14, for use in obtaining a measure of the kaolin concentration by detecting light which has passed through suspension in the chamber 4 in the absence of the alternating electric field. This could be achieved by using a photo-diode assembly which includes more than one photo-diode—see FIG. 4 in which reference numeral 16 denotes a first photo-diode of such an assembly, offset from the axis 14 for detecting scattered light due to deflocculated particles, and reference numberal 17 denotes a second photo-diode of such an assembly for detecting light which has passed through the suspension in the chamber 4, in the absence of an alternating electric field. Outputs from photo-diodes 16 and 17 would then be both applied to the device 15 for subsequent processing.

The device 15 could be an appropriately programmed microprocessor for operating on outputs from the photo-diode 13 or photo-diodes 16 and 17 (or an alternative form of photo-detector or photo-detectors), for example for giving an indication of the degree of deflocculation of the kaolin suspension.

Finally, it is to be noted that the glass cell 1 is first treated before use so that neither water nor kaolin sticks to the faces of the chamber 4. This is achieved by dipping the cell 1 in a 10% by volume solution of di-methyl di-chloro-silane in ether and then baking the cell at 120° C.

Figure 6:
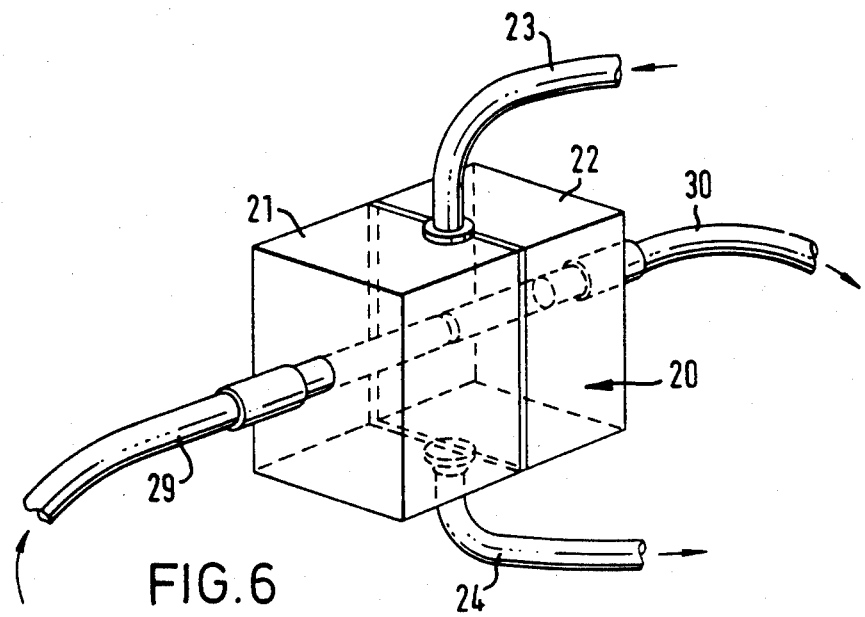
FIG. 6 shows an alternative form of cell.
Figure 7:
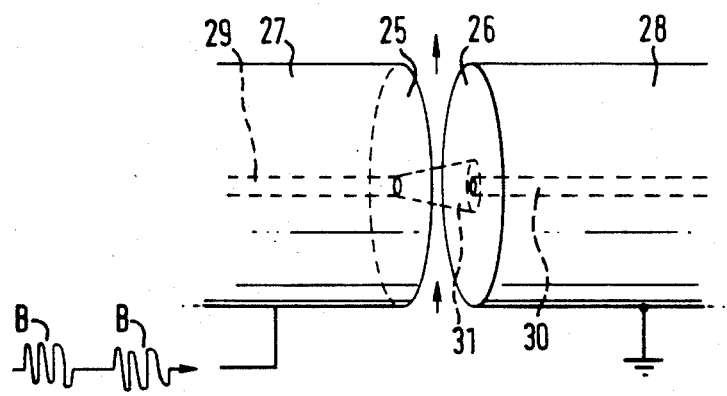
FIG. 7 shows a detail of cell of FIG. 6.

An alternative form of cell and apparatus for use with it will now be described with reference to FIGS. 6 to 9. The cell is shown in FIG. 6 and a detail of it, namely the active region, is shown in FIG. 7. The cell, 20, comprises two glass parts 21 and 22 joined together in a sealed manner with a narrow gap between them through which kaolin suspension flows, via an inlet pipe 23 and an outlet pipe 24.

The spacing between the parts 21 and 22 allows a flow of kaolin suspension to pass by two electrodes 25 and 26 placed in close proximity (typically less than 1 mm). The electrodes are at the ends of ferrules 27 and 28 for optical fibres 29 and 30, the former being for transmitting light from a laser and the latter being for receiving light from the former which has passed through the suspension between the electrodes 25 and 26, reference numeral 31 designating the path of such light.

The electrodes are placed to produce a uniform electric field across the suspension when a voltage difference is applied. In use, bursts B of 50 Hz oscillation are applied to the electrode 25, typically 50 volts r.m.s. Let into each electrode is a respective one of the optical fibres such that at the electrode surface an optical window is created and light can pass from the fibre to the suspension or vice versa. The fibres and electrodes are positioned on a common axis so that light coupled out of one fibre surface into the suspension is recoupled optimally back into the other fibre in the opposite electrode. By this means, the detection of low angle scattered light from the suspension can be achieved by passing a light beam in at fibre 29 and detecting the light coupled into the other. Each of the parts 21 and 22 could be disc-shaped instead of square as shown.

When a voltage is applied to the cell, the polarizeable particles will align with the applied field. Due to the flow of particles in the suspension which continues during the field application, the optically sensed volume becomes filled with aligned particles and, as a result, the low angle scattering properties change. This change is detected in the scattered light between no field and applied field situations. The relative number of electrically polarizeable particles in the suspension and the extent of their polarizeability is dependent upon the degree of deflocculation of the suspension and thus the intensity of the change may be used to differentiate the flocculation state. This is because it is a common situation for flocculated particles to form in combinations that cancel the individual polarizeabilities of the constituent particles.

As no particles align actually in the optical probe due to its being non-conductive, the flow must be utilised to carry the aligned particles into the probe volume and out whilst not materially affecting the particle alignment. This is achieved by using a flow that gives an average particle residence time short compared to the rotary diffusion time of the particles under both application and removal of the field.

The flow speed must be maintained uniform and this is achieved by use of a peristaltic pump of the slow rotation two roller variety where the time of field application is geared to stable points in the pump's delivery characteristic. This is particularly conveniently achieved by the use of an optical reflective sensor that indicates by detection of marks on the pump shaft the appropriate times for measurement.

As the detection scheme is differential, measuring the change in scattering from the suspension when a field is applied, it is convenient to use a pulsed electrical supply. The repetition rate, duration and voltage applied may all be arbitrary but there are particularly convenient setting ranges for each. The repetition rate is set by the triggering signal received from the flow pump. This signal indicates the most frequent repetition of stable flow conditions that is possible. The duration of the applied field must be long enough to allow the particles to fully saturate in terms of the degree of orientation they will achieve and allow a stable measurement of this final value. The longest time is set by the joint effect of pulse duration and field strength that cause sample heating within the electode area to an unacceptable degree.

The supply voltage may be either DC or AC, the particles aligning due to differing aspects of the electric polarizeability in each. It is particularly advantageous to use AC as it minimises the degradation of electrodes through electrolysis. For similar reasons it is convenient to "zero-crossing switch" the AC supply to ensure that no residual DC field is supplied as a result of applying incomplete cycles. The AC field can in general be of arbitrary frequency but it is convenient to use 50 cycles or 60 cycles, deriving the AC field from the incoming live supply. It is also convenient to use an electrode spacing such that the field required may be generated using lower voltages than the line supply.

The applied field has the effect of partially orienting the particles, an effect dependent upon the balance between the polarization induced aligning torque and the effects or Brownian motion. This alignment changes the scattering properties of the sample so that light scattered at any angle is modified in intensity. A detector converts this optical signal to an electronic response which might look as FIG. 8 (for an AC field). With no field applied, an essentially constant measured light intensity is obtained Vb that corresponds to the average scattering of the particles in random orientation. On application of a burst of AC, a new averge value Vs is obtained on which is generally super-imposed an AC signal of twice the supply frequency, Vac. The size of the AC signal component is related to the ratio of the permanent and induced electric dipole moments of the particles. As the state of deflocculation of the clay changes, only small changes occur in the ratio of Vac to Vs. Thus both signals, or a combination, contain information about the state of deflocculation of the clay. It is advantageous however to use the analysis technique that gives maximum resistance to experimental error or fluctuations (such as bubbles, inhomogeneities etc. in the sample). To this end, the area under the burst response (A in FIG. 8) is used to indicate its "size".

The measurement of the sample via a single burst is feasible but restricts the information to that contained in the sample cell during the burst. As samples will contain inhomogeneities of constitution, some of which may be missed in a single burst, it is also advantageous to average the measurement over many bursts.

The technique operates as a measurement of light scattering intensities and so is subject to errors due to loss of optical efficiency through problems with the apparatus. These may reduce the amount of light received through no mechanism of the sample, giving incorrect estimates of deflocculation. Typical errors might be misalignment of the optics, fouling of the fibre ends in the sample, loss of laser power etc. These errors can be almost entirely eliminated by electronic compensation where the optical gain of the system is measured and the electronic gain adjusted to keep the overall combination constant. The optical gain may be conveniently measured by use of the Vb signal available between bursts. If this signal decreases, for example due to laser power fading, the Vb signal falls and the electronic gain adjusts to bring it back to its former value.

In this way, the measurement of the area A can be made largely independent of the optical efficiency and increases the ruggedness of an instrument based on such techniques.

Figure 8:
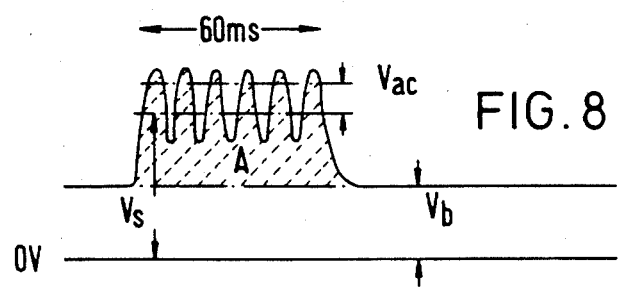
FIG. 8 shows an output of a detector of the cell of FIG. 6.

A further advantage of this gain control is obtained where the sample concentration is such that Vb and A track linearly with concentration fluctuations. Here the gain control operates in such a way that the deflocculation response is made independent of concentration fluctuations. The signal reported as deflocculation response is given below:

$$DR = K \sum_{i=1}^{N} \frac{A_i}{V_{bi}} = K.N. \left( \frac{\bar{A}}{\bar{V_b}} \right)$$

where
K is an instrument scaling factor
N is the number of bursts averaged over
A is the area defined in FIG. 8
Vb is the background signal defined in FIG. 8
$\bar{A}$ is the average of A.

Figure 10:
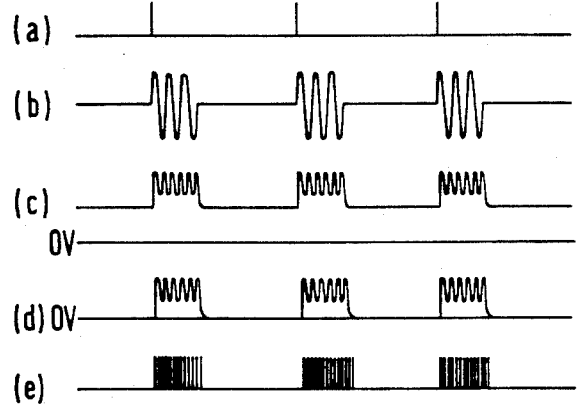
FIG. 10 shows waveforms occurring in the apparatus of FIG. 9.
Figure 9:
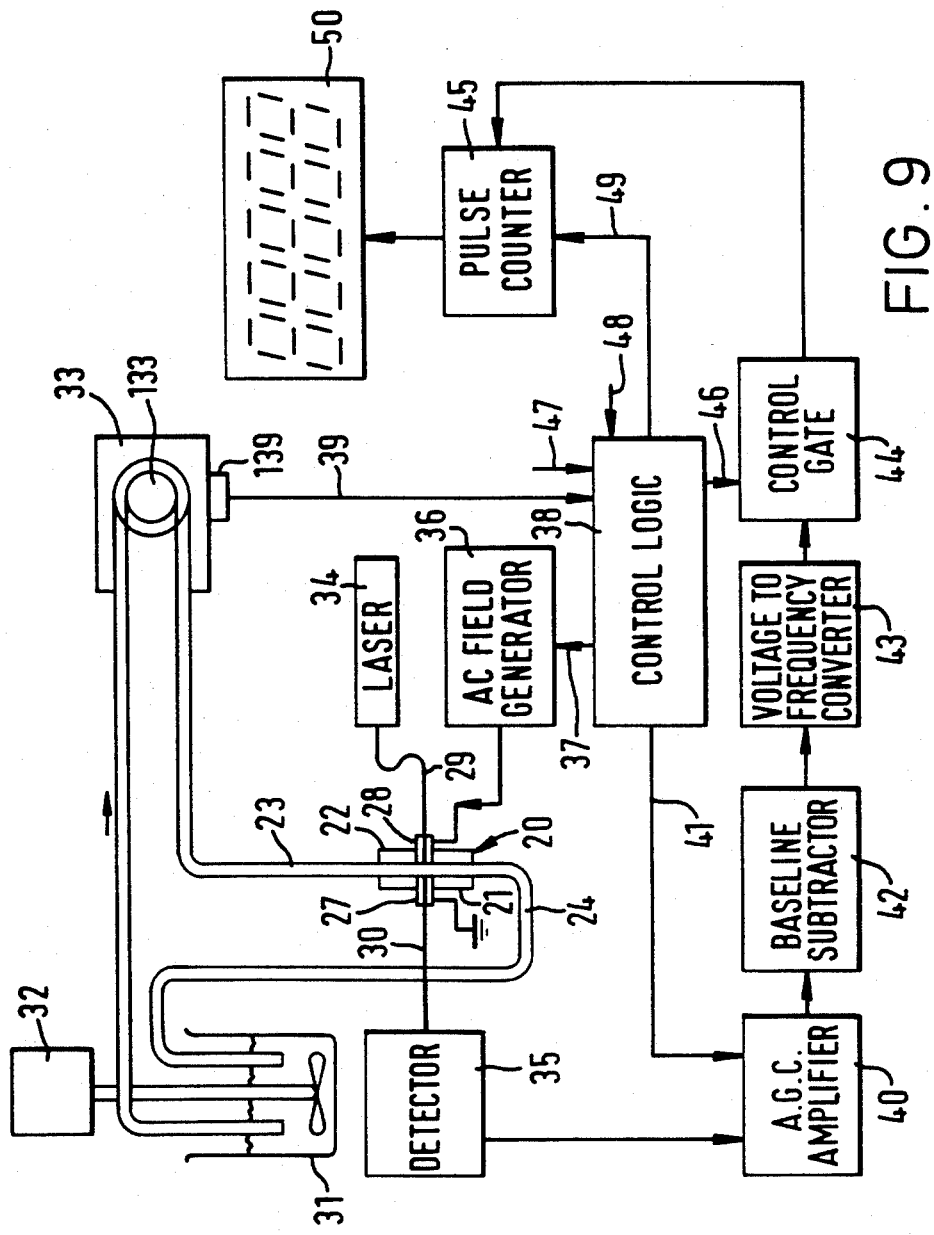
FIG. 9 is a block diagram of apparatus for use with the cell of FIG. 6.

With reference to FIGS. 9 and 10, there will now be described apparatus operating on the basis of the above and using a cell in accordance with FIGS. 6 and 7.

Suspension to be monitored is contained in a sample reservoir 31 and is stirred by a stirrer 32. Supension is pumped through the cell 20 by a peristaltic pump 33 and light is applied to the fibre 29 by a laser 34, the fibre 30 feeding light to a detector 35. An AC field generator 36 is provided for supplying bursts of AC to the electrode 26. The generator 36 generates each burst in response to an input on a line 37 from control logic 38 which is fed with trigger pulses on a line 39, these pulses being produced from an optical reflective sensor 139 that detects marks on the shaft 133 of pump 33. Each field generation input on line 37 is produced in response to a respective trigger pulse on line 39—see FIG. 10a which shows trigger pulses and FIG. 10b which shows AC field bursts applied to electrode 26.

A typical output of the detector 35 is shown by FIG. 10c, and this is applied to an automatic gain control (A.G.C.) amplifier 40, the gain of which is controlled by an output from control logic 38 on a line 41 dependent on the background signal Vb described above. The output of amplifier 40 is applied to a baseline subtractor 42 so that it is clamped to zero, a typical output of subtractor 42 being shown by FIG. 10d. This output is applied to a voltage to frequency converter 43, whose output (a typical example of which is shown by FIG. 10e) is applied to a control gate 44. To provide a response related to the degree of deflocculation, the total number of pulses in the bursts of pulses from the converter 43 are counted for a given number of bursts by a pulse counter 45, the gate 44 being kept open for this number of bursts by a command on a line 46 from control logic 38. Reference numeral 47 denotes an input line to start and reset the counter 45; reference numeral 48 denotes an input line to set the given number of bursts for which pulse counting is to take place; and reference numeral 49 denotes a reset line for the counter 45. Finally, a value for the degree of deflocculation is displayed on a deflocculation response display 50.

The above described forms of apparatus may be used to determine how much deflocculant must be added to a given suspension by taking a sample of the suspension and gradually adding amounts of deflocculant until there is substantially no increase in the indication of the degree of deflocculation, so as to determine the lowest amount of deflocculant per unit volume of suspension that needs to be added to the suspension to substantially fully deflocculate it. Also with no applied field, the concentration of a suspension may be monitored.

Figure 11:
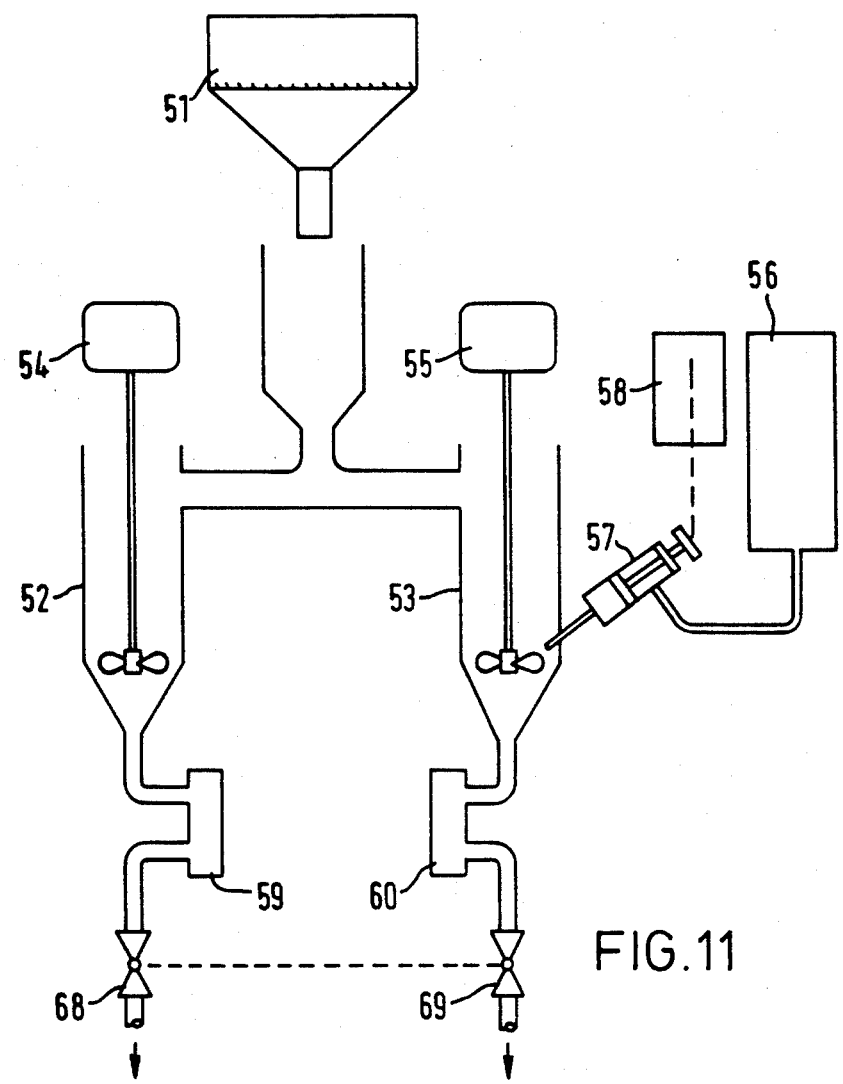
FIG. 11 shows part of apparatus according to the present invention for comparing a test suspension with a reference suspension.
Figure 12:
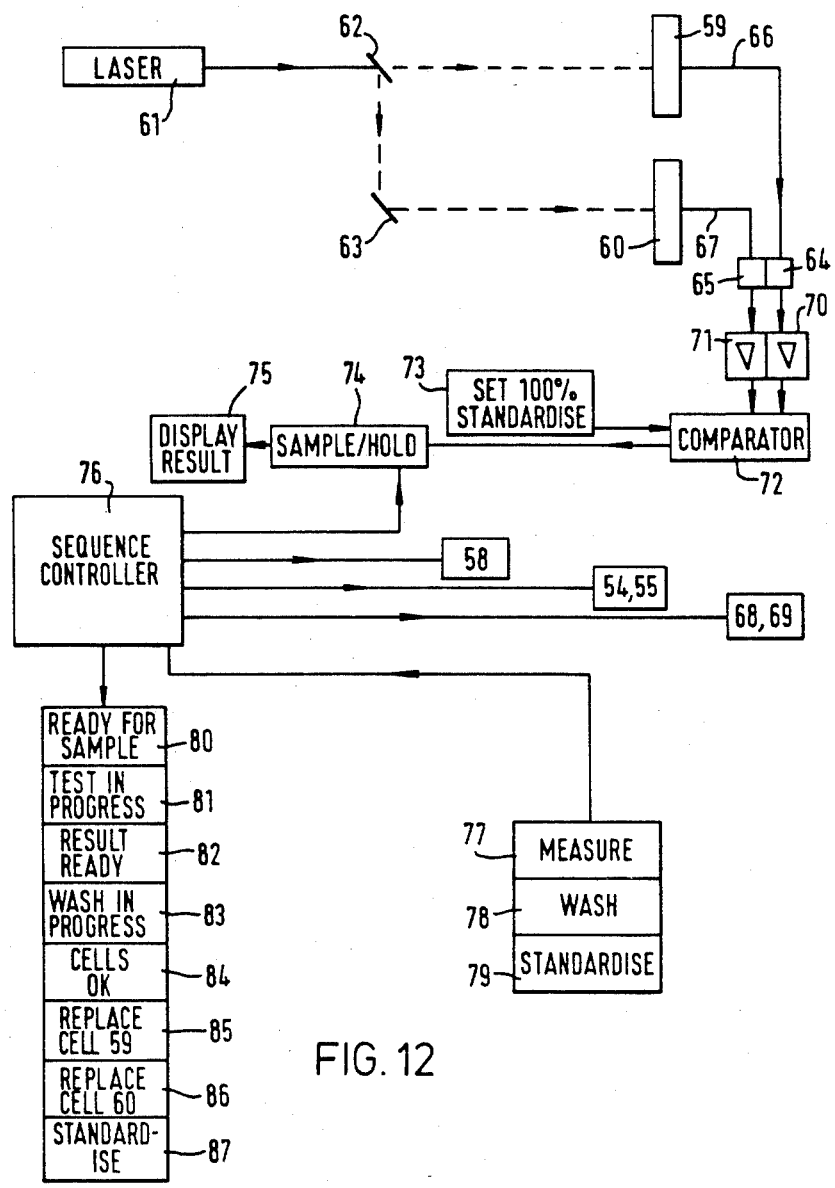
FIG. 12 is a block diagram showing the control system of the apparatus.

With reference to FIGS. 11 and 12, there will now be described apparatus for monitoring the degree of deflocculation of a given sample of suspension by comparing the response it produces using transient electric field light scattering with the response from a sample known to be substantially fully deflocculated.

The apparatus includes an input vessel 51 having a demountable sample screen and into which is poured a fixed volume of sample; two chambers 52 and 53 into which the sample is divided into respective parts; two low speed stirrers 54 and 55 for stirring the parts of the samples in the chambers 52 and 53; a deflocculant reservoir 56; a dose injector 57 for injecting a dose of deflocculant into the part of the sample in chamber 53 from the reservoir 56 under the control of a dose injector actuator 58; two cells 59 and 60 each in accordance with FIGS. 2, 3 and 4 or FIGS. 6 and 7, namely with associated electrodes and field application means; a laser 61 whose beam is divided by a beam splitter 62 so that one part of it is transmitted to the cell 59 and its other part is transmitted (via a mirror 63) to the cell 60; a pair of photo-detectors 64 and 65 for detecting light from output optical fibres 66 and 67 of the cells 59 and 60 respectively; and a pair of mechanically linked solenoid-operated valves 68 and 69 for draining away the parts of the sample in the chambers 52 and 53.

For processing the outputs of the photo-detectors 64 and 65, the apparatus includes the following circuitry, namely: a pair of amplifiers 70 and 71 for amplifying the outputs of the detectors 64 and 65; a comparator 72 receiving the outputs of the amplifiers; a circuit 73 for providing a "set 100% standardise" input to the comparator 72; a sample and hold circuit 74 for receiving the output of the comparator 72; a display 75 for displaying the result; and a sequence controller 76, having an output connected to the sample and hold circuit 74, an output connected for operating the dose injector actuator 58, an output connected for operating the stirrers 54 and 55 and an output for use in opening the valves 68 and 69. There are three push button input switches for actuation by an operator, namely a switch 77 for initiating the measurement sequence, a switch 78 for initiating a wash action and a switch 79 for setting the "standardise" operation. Finally, there is a set of indicating lamps fed by the sequence controller 76, namely a lamp 80 indicating that the apparatus is ready for a sample; a lamp 81 indicating that a test is in progress; a lamp 82 indicating that the result is ready; a lamp 83 indicating that a wash is in progress; a lamp 84 for indicating that the cells 59 and 60 do not have their windows fouled and/or are not blocked; lamps 85 and 86 for indicating that cell 59 or 60 respectively should be replaced; and a lamp 87 for indicating that "standardising" is taking place.

The apparatus is used as follows:

A sample of kaolin suspension is poured into the vessel 51, the screen is removed and washed and the switch 77 pressed. The sequence is then automatic under the control of the sequence controller 76, the stirrers 54 and 55 being put on; an overdose of deflocculant being added to the part of the sample in the chamber 53 from the reservoir 56 via the injector 57 under the control of the actuator 58, a short wait of 30 seconds occurring, the particles in the part of the sample to which defloccuant has been added becoming fully deflocculated; the valves 68 and 69 being opened; the measurement being carried out; and the result of comparison being indicated on display 75, the lamp 82 coming on. The operator then puts water in and presses the switch 77, the sequence then becoming automatic again, the stirrers 54 and 55 coming on; a short wait of 10 seconds occurring; the valves 68 and 69 being opened; and a check occurring as regards cell window fouling and/or a blocked cell, lamp 84 coming on if the check is satisfactory.

To standardise the apparatus, the operator puts in a clay sample and presses the switch 79. The above measurement sequence is run but without the overdose for referencing purposes. The operator is requested to set standardise to 100% by lamp 87 coming on (or standardising is done automatically).

The measurement sequence should be as follows: apply the field (in the example an alternating electric field) as a pulse (e.g. 10-20 ms long); store the results; wait 5-10 seconds; repeat, say 10 times; and output an average result.

It may be possible to use the DC (non-applied field) levels as a continuous standardise level or even as a total amount of solids indication.

As an alternative to two cells, a single cell could be used, the measured and reference (overdosed) samples being passed through in sequence.

I claim:

1. A method of monitoring the deflocculation of particles in a liquid suspension, which particles, when deflocculated, are such that they can become aligned in an applied field, the method comprising supplying the suspension to a monitoring region applying a beam of radiation to the suspension in said region, applying a disturbance field to the said region, said field being in a direction parallel to the direction of said beam of radiation, and detecting a change, if any, in the forward radiation scattering properties of the suspension with respect to the beam in said region due to the aligning of deflocculated particles of said suspension in said field, the method further comprising applying such a field to such a region of a first sample of suspension whose degree of defloccation is desired to be monitored and applying such a field to such a region of a second sample of suspension, whose particles are known to be substantially fully deflocculated, detecting the change in radiation scattering properties of each region due to the field to produce a respective output indication, and comparing the indications to produce an indication related to the degree of deflocculation of the particles in the first suspension.

2. A method according to claim 1, wherein said field is an electric field.

3. A method according to claim 2, wherein said electric field is an alternating electric field.

4. A method according to claim 1, wherein said beam of radiation is a beam of light.

5. A method according to claim 4, wherein said light is applied from a laser.

6. A method according to claim 1, wherein said suspension is passed through a cell which is transparent to said radiation and provides said region in which said field is produced and on to which region said radiation is applied.

7. A method according to claim 6, wherein said cell incorporates a pair of electrodes for producing said field as an electric field in said region and is associated with detection means for detecting such radiation, for producing an indication related to said change, if any.

8. Apparatus for monitoring the deflocculation of particles in a liquid suspension, which particles, when deflocculated, are such that they can become aligned in an applied field, the apparatus comprising first means, for providing a monitoring region into which at least a part of said suspension is supplied; second means for applying a beam of radiation to said region; third means, for producing a disturbance field in said region, said field being in a direction parallel to the direction of said beam of radiation, and fourth means, for detecting a change, if any, in the forward radiation scattering properties of the suspension with respect to the beam in said region due to the aligning of deflocculated particles of said suspension in said region, said third means being suitable for applying such a field to such a region of a first sample of suspension whose degree of deflocculation is desired to be monitored and for applying such a field to such region of a second sample of suspension, whose particles are known to be substantially fully deflocculated, said fourth means being suitable for detecting the change in radiation scattering properties of each region due to the field to produce a respective output indication and the apparatus further comprising means for comparing the indications to produce an indication related to the degree of deflocculation of the particles in the first suspension.

9. Apparatus according to claim 8, wherein said field is an electric field.

10. Apparatus according to claim 9, wherein said electric field is an alternating electric field.

11. Apparatus according to claim 8, wherein said second means is means for applying a beam of light.

12. Apparatus according to claim 11, wherein said second means comprises a laser.

13. Apparatus according to claim 8, wherein said first means comprises a cell which is transparent to said radiation and through which said suspension is passed and provides said region in which said field is produced and on to which region said radiation is applied.

14. Apparatus according to claim 13, wherein said third means comprises a pair of electrodes incorporated with said cell for producing said field as an electric field in said region, said fourth means comprising detection means associated with said cell for detecting such radiation, for producing an indication related to said change, if any.

* * * * *